US008664431B2

(12) United States Patent
Loccufier

(10) Patent No.: US 8,664,431 B2
(45) Date of Patent: Mar. 4, 2014

(54) PREPARATION METHOD OF COPOLYMERIZABLE PHOTOINITIATORS

(75) Inventor: Johan Loccufier, Zwijnaarde (BE)

(73) Assignee: Agfa Graphics NV, Mortsel (BE)

( * ) Notice: Subject to any disclaimer, the term of this patent is extended or adjusted under 35 U.S.C. 154(b) by 685 days.

(21) Appl. No.: 12/744,966

(22) PCT Filed: Nov. 27, 2008

(86) PCT No.: PCT/EP2008/066289
§ 371 (c)(1),
(2), (4) Date: May 27, 2010

(87) PCT Pub. No.: WO2009/068590
PCT Pub. Date: Jun. 4, 2009

(65) Prior Publication Data
US 2010/0305336 A1    Dec. 2, 2010

Related U.S. Application Data

(60) Provisional application No. 60/991,381, filed on Nov. 30, 2007.

(30) Foreign Application Priority Data

Nov. 29, 2007   (EP) .................................... 07121832

(51) Int. Cl.
*C07C 69/63*   (2006.01)
(52) U.S. Cl.
USPC ....................................................... 560/228
(58) Field of Classification Search
USPC ....................................................... 560/228
See application file for complete search history.

(56) References Cited

U.S. PATENT DOCUMENTS

| 4,329,360 | A | 5/1982 | Resnick |
| 4,922,004 | A | 5/1990 | Köhler et al. |
| 5,837,746 | A | 11/1998 | Köhler et al. |

FOREIGN PATENT DOCUMENTS

| ES | 8604903 A1 | 8/1986 |
| GB | 890214 A | 2/1962 |
| GB | 2 328 207 A | 2/1999 |
| JP | 2004-182949 A | 7/2004 |
| WO | 95/07879 A1 | 3/1995 |

OTHER PUBLICATIONS

Flohr et al Angewandte Chemie 1976, 88, 613-14—abstract.*
Official Communication issued in International Patent Application No. PCT/EP2008/066289, mailed on Apr. 15, 2009.
Buruiana et al., "Synthesis of polyetherurethane cationomers with anthraquinone structure", European Polymer Journal, pp. 2505-2511, vol. 37, 2001.
Gilbert et al., "Dehydrobromination of Some Substituted Phenyl 3-Bromopropionates and Phenyl 3-Bromothiolopropionates. Transmission of Activation Effects through Acyl Bonds", Journal of Organic Chemistry, 1983, pp. 2724-2728, vol. 48.
McMorris et al., "Studies on the Pterosins and Other Indanones Related to the Illudins", ISSN: 0024-5461, 1977, pp. 221-224.
Valters et al., "Synthesis and properties of 2-(omega-aminoacyloxymethyl)-2-aryl-1, 3-indandione", No. 1968:443643 ISSN, pp. 1-2.
Akdag et al., "Manganese(III) acetate oxidation of some ketones in the presence of 3-chloropropionic acid and theoretical investigation of the products", Journal of Molecular Structure THEOCHEM 571, 2001, pp. 201-206, ISSN: 0166-120.
Database Beilstein (online), Beilstein Institute for organic chemistry, Database accession No. 2696576 abstract & Kawanaga, 1994, p. 210, vol. 23, 2 pages.

* cited by examiner

*Primary Examiner* — John Mabry
(74) *Attorney, Agent, or Firm* — Keating & Bennett, LLP

(57) ABSTRACT

An intermediate for preparing (meth)acrylated photoinitiators according to Formula (I):

$$\left(X\diagdown\underset{\underset{O}{\|}}{\overset{R1}{\diagup}}\hspace{-2pt}O\right)_{n}\hspace{-4pt}\text{L}\hspace{-4pt}\left(A\right)_{o}$$

Formula (I)

wherein:
R1 is selected from the group consisting of hydrogen and a methyl group;
A represents a group including at least one photoinitiating moiety;
L represents a n+o-valent linking group including at least one carbon atom;
n and o each independently represent an integer from 1 to 4;
p is equal to 0 or 1;
X represents a group selected from the group consisting of Cl, Br, I, and $R^2SO_3$; and
$R^2$ represents an optionally substituted group selected from the group consisting of an alkyl group, an alkenyl group, an alkynyl group, an alkaryl group-, an aralkyl group, an aryl group and a heteroaryl group. Also, a method for the preparation of (meth)acrylated photoinitiators by β-elimination of HX from the intermediate according to Formula (I).

5 Claims, No Drawings

PREPARATION METHOD OF COPOLYMERIZABLE PHOTOINITIATORS

CROSS-REFERENCE TO RELATED APPLICATIONS

This application is a 371 National Stage Application of PCT/EP2008/066289, filed Nov. 27, 2008. This application claims the benefit of U.S. Provisional Application No. 60/991,381, filed Nov. 30, 2007, which is incorporated by reference herein in its entirety. In addition, this application claims the benefit of European Application No. 07121832.5, filed Nov. 29, 2007, which is also incorporated by reference herein in its entirety.

BACKGROUND OF THE INVENTION

1. Field of the Invention

The present invention relates to new intermediates for the preparation of (meth)acrylated photoinitiators and to a method for the preparation of (meth)acrylated photoinitiators.

2. Description of the Related Art

A free radical photoinitiator is a chemical compound that initiates a polymerization of monomers when exposed to actinic radiation by the formation of a free radical. Photoinitiators are frequently used in UV-curable compositions, such UV curable inkjet inks.

For coating or printing on food packaging materials, it can be necessary to use a copolymerizable photoinitiator due to the possible or known toxicity of a photoinitiator and its degradation products.

U.S. Pat. No. 4,922,004 (MERCK) discloses acryloyloxyphenyl hydroxypropyl ketones and other types of copolymerizable photoinitiators. These photoinitiators are prepared using (meth)acryloyl chloride.

It is commonly known that (meth)acryloyl chloride is highly reactive and limited in stability. It is often contaminated with cyclic dimers requiring destillation prior to use. Combined with the highly toxic nature of (meth)acryloyl chloride, the limited availability on the market and the high cost, synthetic methods using (meth)acryloyl chloride are not well suited for the preparation of (meth)acrylated photoinitiators on an industrial scale.

Acrylates and methacrylates in general can be prepared, using different synthetic strategies. Classically, acid catalyzed esterification of acrylic or methacrylic acid with the required alcohol is used. However, this method is incompatible with acid sensitive functional groups as e.g. in several α-hydroxy-ketone photoinitiators, requiring a different synthetic strategy.

It is highly desirable to be able to obtain (meth)acrylated photoinitiators with high purity, according to a simplified process compared to state of the art processes, avoiding the highly reactive, unstable and toxic (meth)acryloyl chloride.

SUMMARY OF THE INVENTION

Preferred embodiments of the present invention provide new versatile intermediates for the preparation of (meth)acrylated photoinitiators.

A further preferred embodiment of the present invention provides a method for the preparation of (meth)acrylated photoinitiators according to a simple process on an industrial scale.

A further preferred embodiment of the present invention provides a method for the preparation of (meth)acrylated photoinitiators according to a process not requiring (meth)acryloyl chloride.

These and other preferred embodiments of the invention will become apparent from the description hereinafter.

A very simple method for the preparation of (meth)acrylated photoinitiators has been found by β-elimination of HCl from a new type of intermediate in an aprotic solvent using a suspension of an inorganic base or a salt of a carboxylic acid. The preparation yielded (meth)acrylated photoinitiators with high purity and avoided the use of highly reactive, unstable and toxic (meth)acryloyl chloride.

A preferred embodiment of the invention has been realised with an intermediate as defined below.

A preferred embodiment of the invention has also been realised with a method for preparation of an intermediate as defined below.

Other preferred embodiments of the invention have also been realised with a method for preparation of (meth)acrylated photoinitiators as defined below.

Further advantages and preferred embodiments of the present invention will become apparent from the following description.

DETAILED DESCRIPTION OF THE PREFERRED EMBODIMENTS

Definitions

The term "UV" is used in disclosing the present application as an abbreviation for ultraviolet radiation.

The term "actinic radiation" as used in disclosing the present invention, means electromagnetic radiation capable of initiating photochemical reactions.

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methylbutyl etc.

The term "substituted" as used in disclosing this invention means that one or more of the carbon atoms and/or that a hydrogen atom of one or more of the carbon atoms in an aliphatic group (such as an alkyl group, an alkene group and an alkyn group), an aromatic group (such as an aralkyl group and a alkaryl group) or an alicyclic hydrocarbon group, are replaced by an oxygen atom, a nitrogen atom, a phosphorous atom, a silicon atom, a sulfur atom, a halogen atom, a selenium atom or a tellurium atom, or a group containing one or more of these said carbon and hydrogen replacing atoms. Such substituents include hydroxyl groups, thiol groups, carbamate groups, urea groups, ether groups, thioether groups, carboxylic acid groups, ester groups, sulphonate groups, sulphonamide groups, phosphonate groups, phosphonamide groups, phosphonamidate groups, amide groups and amine groups.

The term "heteroaryl group" means an aromatic group wherein at least one of the cyclic conjugated carbon atoms is replaced by a sulfur atom, an oxygen atom, a selenium atom, a nitrogen atom or a phosphorous atom. A heteroaromatic group is considered a synonym of heteroaryl group.

Methods for the Preparation of (Meth)Acrylated Photoinitiators

Acrylates and methacrylates can be prepared using different synthetic pathways. Usually, acid catalyzed esterification of acrylic or methacrylic acid with the required alcohol is used. This method is incompatible with acid sensitive functional groups as e.g. in several α-hydroxy-ketone photoinitiators.

In the present invention, a β-elimination in an aprotic solvent using an inorganic base, as illustrated by the synthetic scheme I below, is used as the synthetic approach for the preparation of acrylated or methacrylated photoinitiators including acid sensitive functional groups. However, the method is also suitable for the preparation of acrylated or methacrylated photoinitiators lacking acid sensitive functional groups.

Synthetic scheme I:

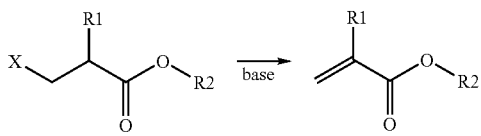

wherein:
X is selected from the group consisting of Cl, Br, I and a sulfonate ester; R1 represents hydrogen or a methyl group; and R2 a photoinitiating moiety including an acid sensitive functional group.

In the preparation of (meth)acrylates, WO 95/07879 (ALLIED COLLOIDS) discloses tertiary amines as the preferred hydrogen halide acceptors. A further disclosure can be found in EP 133164 A (CIBA), where the use of triethyl amine is disclosed in the examples. The use of nitrogen-containing basic compounds or inorganic hydroxides in the preparation of sulfur-containing (meth)acrylates via β-elimination is disclosed in U.S. Pat. No. 5,916,987 (MITSUI CHEMICALS).

Copolymerizable photoinitiators including acid sensitive functional groups or hydrolytically labile functional groups could be prepared by using as the starting compound of Synthetic scheme I, the intermediate according to Formula (I):

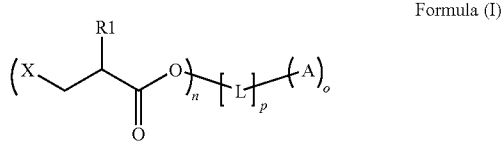

Formula (I)

wherein:
R1 is selected from the group consisting of hydrogen and a methyl group;
A represents a group including at least one photoinitiating moiety;
L represents a n+o-valent linking group including at least one carbon atom;
n and o each independently represent an integer from 1 to 4;
p is equal to 0 or 1;
X represents a group selected from the group consisting of Cl, Br, I and $R^2SO_3$; and
$R^2$ represents an optionally substituted group selected from the group consisting of an alkyl group, an alkenyl group, an alkynyl group, an alkaryl group, an aralkyl group, an aryl group and a heteroaryl group.

The intermediates according to Formula (I) can be prepared by reacting a starting material according to Formula (II) with an acid chloride according to Formula (III), in an aprotic solvent using a suspension of an inorganic base or a salt of a carboxylic acid:

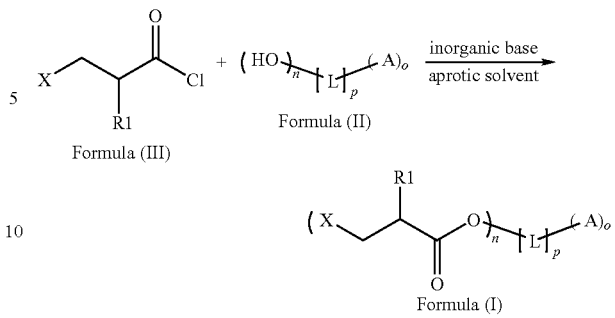

wherein:
R1 is selected from the group consisting of a hydrogen or methyl group;
A represents a group including at least one a photoinitiating moiety;
L represents a n+o-valent linking group including at least one carbon atom;
n and o each independently represent an integer from 1 to 4;
p is equal to 0 or 1;
X represents a group selected from the group consisting of Cl, Br, I and $R^2SO_3$; and
$R^2$ represents an optionally substituted group selected from the group consisting of an alkyl group, an alkenyl group, an alkynyl group, an alkaryl group, an aralkyl group, an aryl group and a heteroaryl group.

In a preferred embodiment, the intermediates according to Formula (I) are prepared by reacting a starting material according to Formula (II) with an acid chloride according to Formula (III), in an aprotic solvent using a suspension of a salt of a carboxylic acid or an inorganic base selected from the group consisting of a carbonate salt, a bicarbonate salt, a borate salt, a phosphate salt and a hydrogen phosphate salt, and directly converted into the corresponding (meth)acrylate under the same circumstances, without isolating the intermediate according to Formula (I).

The linking group L of the intermediate according to Formula (I) preferably does not contain more then 20 carbon atoms.

In a further preferred embodiment of the intermediate according to Formula (I), both n and o are 1. As a consequence, L preferably represents a divalent linking group.

In a further preferred embodiment of the intermediate according to Formula (I), L links A to O via a functional group selected from the group consisting of an ester, an amide, an ether, a thioether and an amine.

In the most preferred embodiment of the intermediate according to Formula (I), L is selected from the group consisting of a substituted or unsubstituted alkylene group, a substituted or unsubstituted arylene group, a substituted or unsubstituted heteroarylene group, an alkylene group being particularly preferred.

Photoinitiating Moieties A

The photoinitiating moiety A in the intermediate according to Formula (I) can be derived from a Norrish Type-I or a Norrish Type-II-initiator.

In a preferred embodiment, the photoinitiating moiety A is selected from the group consisting of benzoinethers, benzil ketals, α,α-dialkoxyacetophenones, α-hydroxyalkylphenones, α-aminoalkylphenones, acylphosphine oxides, bisacylphosphine oxides, acylphosphine sulfides, α-haloketones, α-halosulfones, phenylglyoxalates, benzophenones, thioxanthones, 1,2-diketones and anthraquinones.

Typical examples of photoinitiating moieties A are given by Table 1 without being limited thereto:
TABLE 1
A1 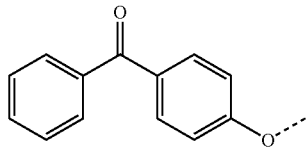
A2 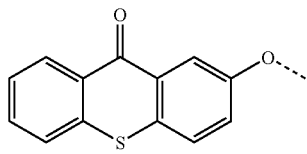
A3 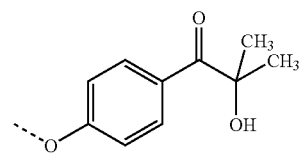
A4 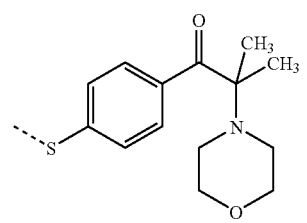
A5 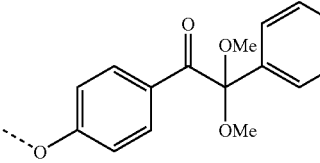
A6 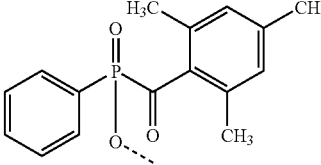
A7 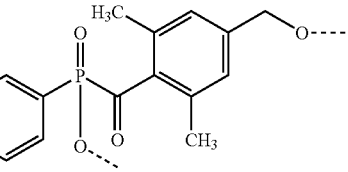
A8 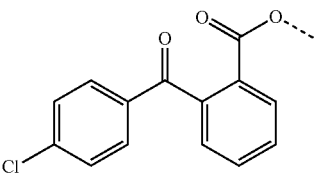
TABLE 1-continued
A9 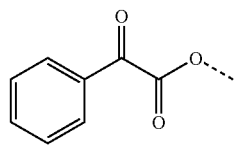
A10 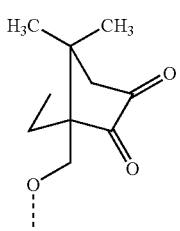
A11 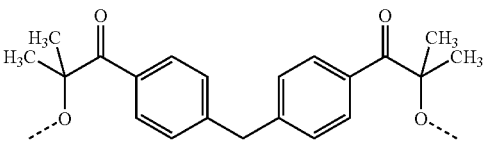
A12 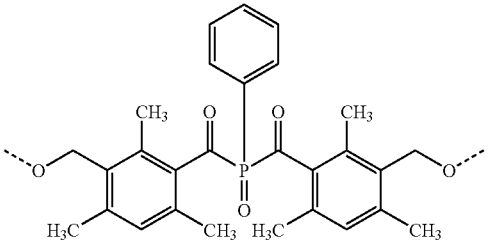
A13 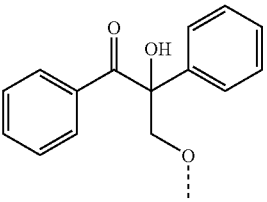
A14 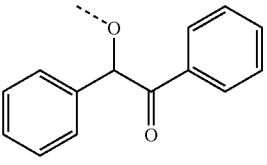
A15 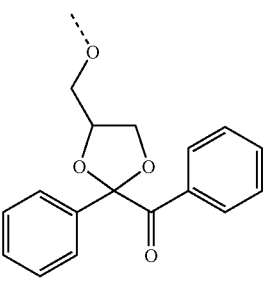
A16 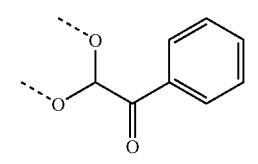

The dotted line represents the bonding site to L in the intermediate according to Formula (I). When p is equal to 0, the oxygen atoms on the photoinitiating moiety A are part of the ester in Formula (I) and the hydroxyl group in Formula (II).

In an even further preferred embodiment, X in the intermediate according to Formula (I) is selected from the group consisting of Cl and Br, Cl being particularly preferred.

Intermediates

Typical intermediates according to the present invention are given by Table 2, without being limited thereto.

TABLE 2

INT-1
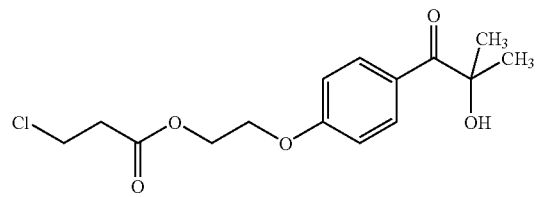

INT-2
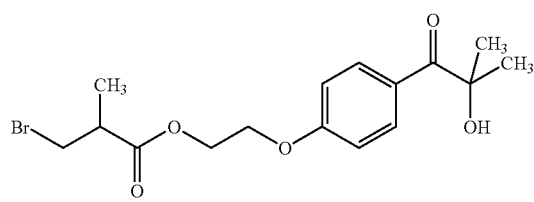 [SMILES: CC(CBr)C(=O)OCCOc1ccc(C(=O)C(C)(C)O)cc1]

INT-3
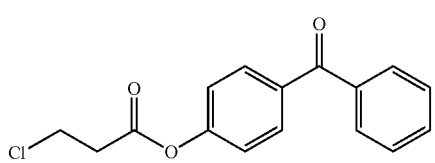 [SMILES: O=C(CCCl)Oc1ccc(C(=O)c2ccccc2)cc1]

INT-4
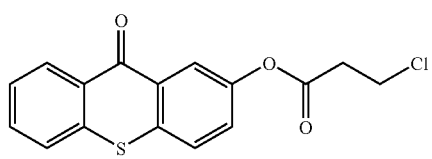 [SMILES: O=C(CCCl)Oc1ccc2sc3ccccc3c(=O)c2c1]

INT-5
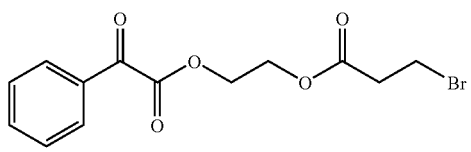 [SMILES: O=C(CCBr)OCCOC(=O)C(=O)c1ccccc1]

INT-6
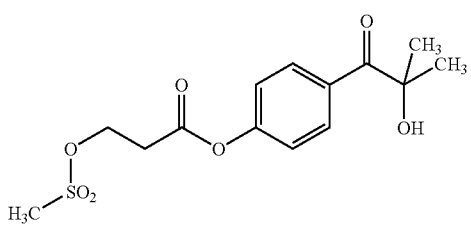 [SMILES: CC(C)(O)C(=O)c1ccc(OC(=O)CCOS(C)(=O)=O)cc1]

INT-7
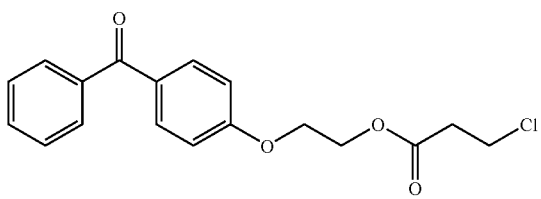 [SMILES: O=C(CCCl)OCCOc1ccc(C(=O)c2ccccc2)cc1]

TABLE 2-continued
INT-8
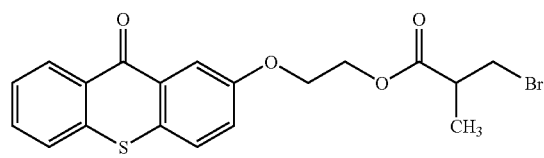 [SMILES: CC(CBr)C(=O)OCCOc1ccc2sc3ccccc3c(=O)c2c1]
INT-9
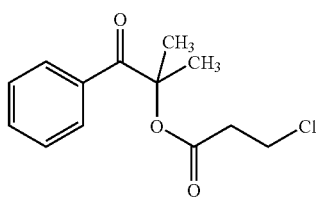 [SMILES: CC(C)(OC(=O)CCCl)C(=O)c1ccccc1]
INT-10
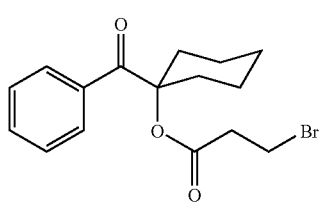 [SMILES: O=C(CCBr)OC1(C(=O)c2ccccc2)CCCCC1]
INT-11
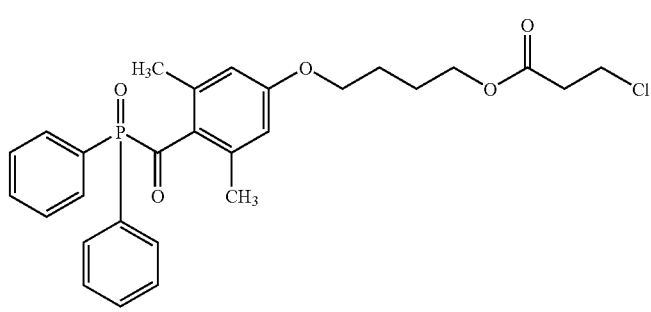 [SMILES: Cc1cc(OCCCCOC(=O)CCCl)cc(C)c1C(=O)P(=O)(c1ccccc1)c1ccccc1]
INT-12
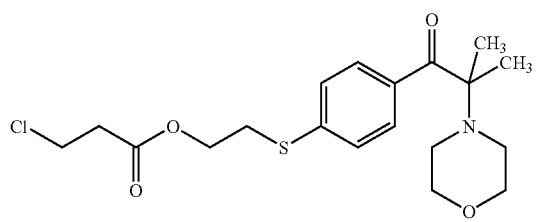 [SMILES: CC(C)(C(=O)c1ccc(SCCOC(=O)CCCl)cc1)N1CCOCC1]
INT-13
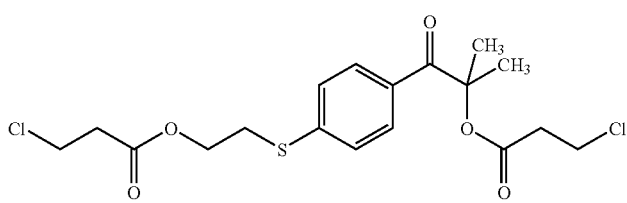 [SMILES: CC(C)(OC(=O)CCCl)C(=O)c1ccc(SCCOC(=O)CCCl)cc1]
INT-14
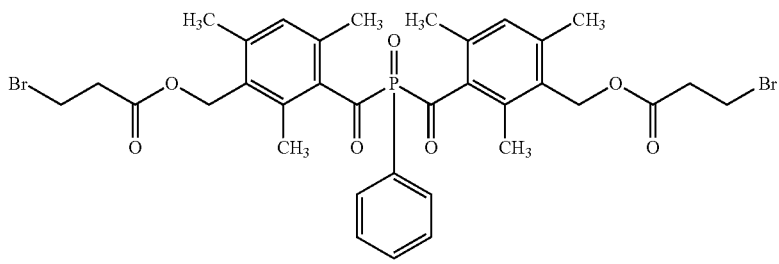 [SMILES: Cc1cc(C)c(C(=O)P(=O)(C(=O)c2c(C)cc(C)c(COC(=O)CCBr)c2C)c2ccccc2)c(C)c1COC(=O)CCBr]

TABLE 2-continued

INT-15
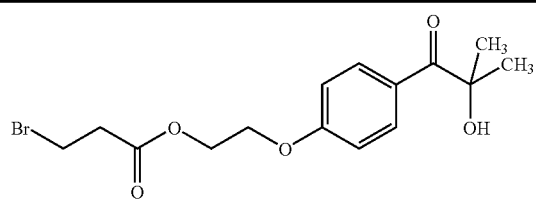

INT-16
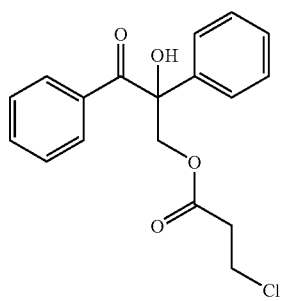 [SMILES: O=C(CCCl)OCC(O)(C(=O)c1ccccc1)c1ccccc1]

INT-17
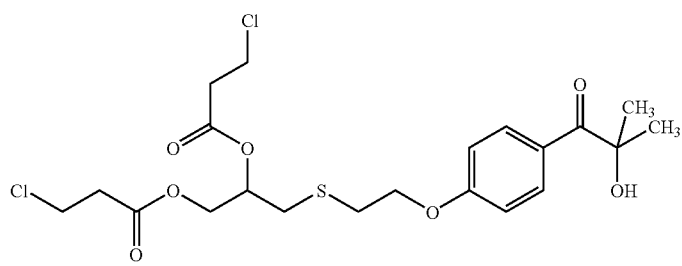 [SMILES: CC(C)(O)C(=O)c1ccc(OCCSCC(COC(=O)CCCl)OC(=O)CCCl)cc1]

INT-18
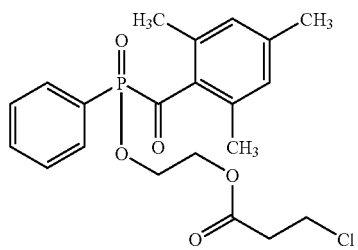 [SMILES: Cc1cc(C)c(C(=O)P(=O)(OCCOC(=O)CCCl)c2ccccc2)c(C)c1]

INT-19
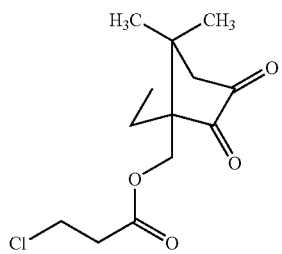 [SMILES: CCC1(COC(=O)CCCl)C(=O)C(=O)CC1(C)C]

INT-20
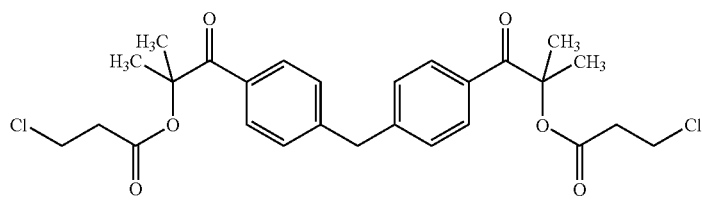 [SMILES: CC(C)(OC(=O)CCCl)C(=O)c1ccc(Cc2ccc(C(=O)C(C)(C)OC(=O)CCCl)cc2)cc1]

The intermediates according to Formula (I) are of particular interest for the preparation of (meth)acrylated photoinitiators. However, the intermediates according to Formula (I) are very versatile starting materials for the synthesis of a wide variety of photoinitiator derivatives as illustrated in the scheme below for INT-1.

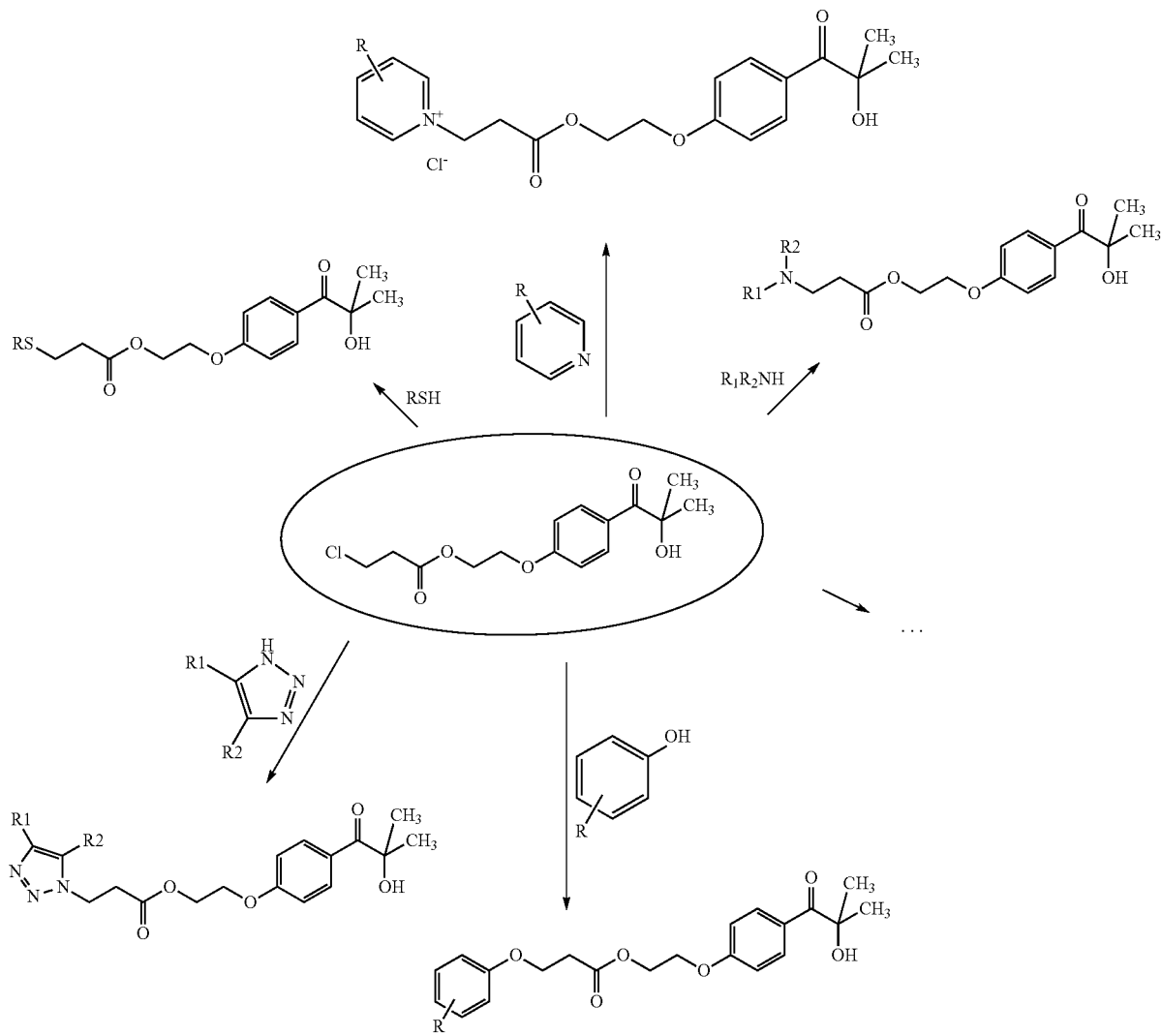

Inorganic Bases and Salts of a Carboxylic Acid

It is essential to use an inorganic base or a salt of a carboxylic acid in the method for the preparation of (meth) acrylated photoinitiators by β-elimination of HX from the intermediate according to Formula (I) in a aprotic solvent. The inorganic base or the salt of a carboxylic acid is preferably present in the form of a suspension.

The suspension of the inorganic base or the salt of a carboxylic acid may be prepared from commercial grades of the different inorganic bases or salts of a carboxylic acid, without further reduction of the particle size. Conventional milling and dispersing techniques can be used to reduce the particle size of the suspension of the inorganic base or the salt of a carboxylic acid, in order to further optimize the synthetic method as disclosed by the present invention, e.g. to increase the reaction speed.

The inorganic base is preferably selected from the group consisting of a carbonate salt, a bicarbonate salt, a borate salt, a phosphate salt and a hydrogen phosphate salt.

In a preferred embodiment the inorganic base or the salt of a carboxylic acid is a potassium salt, i.e. having a potassium counter ion.

In the most preferred embodiment potassium carbonate is used as inorganic base.

The use of a potassium salt has been found to be advantageous in obtaining a high conversion in a short reaction time, compared to, for example, a sodium salt. Organic bases, such as triethyl amine, frequently used in other types of β-elimination reactions, lead to incomplete conversion and/or were more difficult to implement on an industrial scale by a more complex isolation procedure.

Aprotic Solvents

It is essential to use an aprotic solvent in the method for the preparation of (meth)acrylated photoinitiators by β-elimination of HX from the intermediate according to Formula (I) in combination with an inorganic base or a salt of a carboxylic acid.

The aprotic solvent is preferably selected from the group consisting of aliphatic ketones such as acetone and 2-butanone, aliphatic nitriles such as acetonitrile, cyclic ethers such as tetrahydrofurane and dioxane, aliphatic esters, such as ethyl acetate and isopropyl acetate, aliphatic ethers, such as diethyl ether and t-butyl methyl ether, glycol ethers, glycol esters, Proglyde DMM™ from Dow, Dowanol PMA™ from Dow, dimethyl acetamide, dimethyl formamide, N-methylpyrrolidone, dimethyl sulfoxide, sulfolane, lactones such as γ-butyrolactone, halogenated hydrocarbons, such as methylene chloride, aromatic hydrocarbons such as toluene and aliphatic hydrocarbons such as cyclohexane.

Mixtures of two or more different aprotic organic solvents can be used.

Copolymerizable Photoinitiators

Typical initiators that can be prepared according to the method for the preparation of (meth)acrylated photoinitiators according to the present invention are given by Table 3, without being limited thereto.

TABLE 3

INI-1
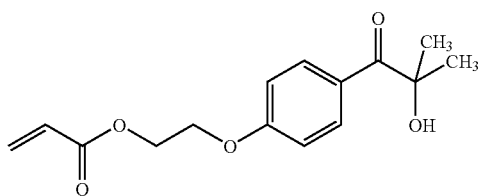 [SMILES: C=CC(=O)OCCOc1ccc(C(=O)C(C)(C)O)cc1]

INI-2
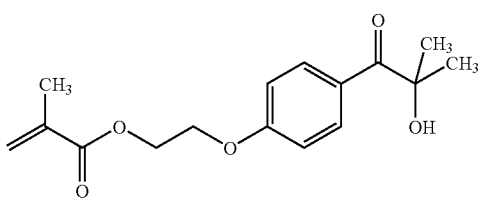 [SMILES: C=C(C)C(=O)OCCOc1ccc(C(=O)C(C)(C)O)cc1]

INI-3
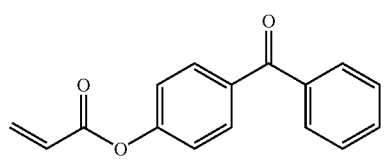 [SMILES: C=CC(=O)Oc1ccc(C(=O)c2ccccc2)cc1]

INI-4
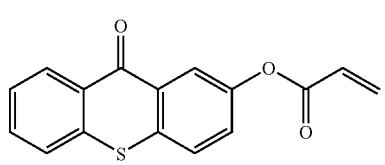 [SMILES: C=CC(=O)Oc1ccc2sc3ccccc3c(=O)c2c1]

INI-5
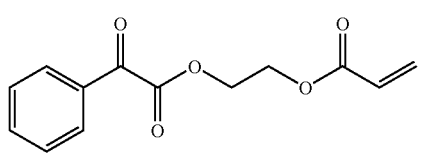 [SMILES: C=CC(=O)OCCOC(=O)C(=O)c1ccccc1]

INI-6
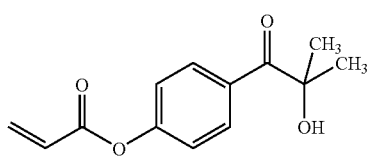 [SMILES: C=CC(=O)Oc1ccc(C(=O)C(C)(C)O)cc1]

INI-7
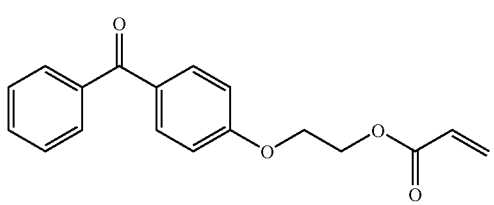 [SMILES: C=CC(=O)OCCOc1ccc(C(=O)c2ccccc2)cc1]

INI-8
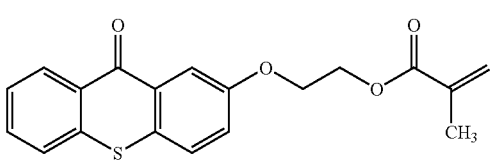 [SMILES: C=C(C)C(=O)OCCOc1ccc2sc3ccccc3c(=O)c2c1]

TABLE 3-continued
INI-9
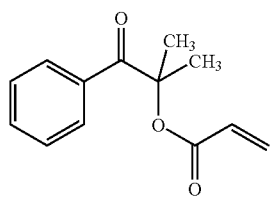 [SMILES: C=CC(=O)OC(C)(C)C(=O)c1ccccc1]
INI-10
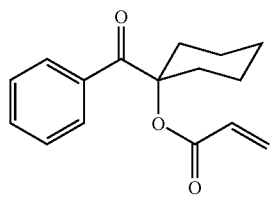 [SMILES: C=CC(=O)OC1(C(=O)c2ccccc2)CCCCC1]
INI-11
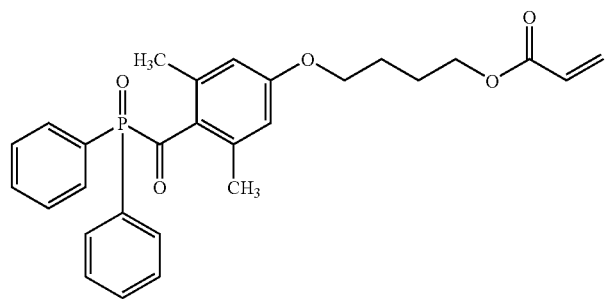 [SMILES: C=CC(=O)OCCCCOc1cc(C)c(C(=O)P(=O)(c2ccccc2)c2ccccc2)c(C)c1]
INI-12
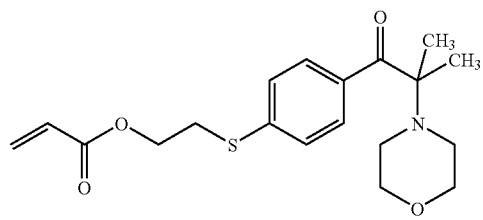 [SMILES: C=CC(=O)OCCSc1ccc(C(=O)C(C)(C)N2CCOCC2)cc1]
INI-13
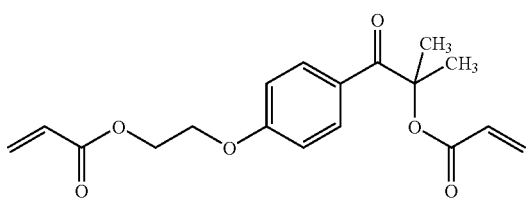 [SMILES: C=CC(=O)OCCOc1ccc(C(=O)C(C)(C)OC(=O)C=C)cc1]
INI-14
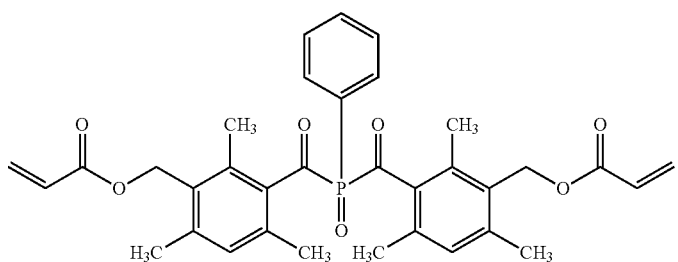 [SMILES: C=CC(=O)OCc1c(C)cc(C)c(C(=O)P(=O)(C(=O)c2c(C)cc(C)c(COC(=O)C=C)c2C)c2ccccc2)c1C]

TABLE 3-continued
INI-15
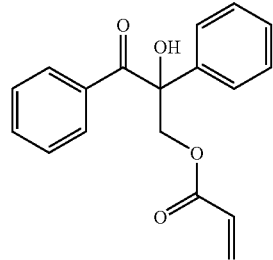 [SMILES: C=CC(=O)OCC(O)(C(=O)c1ccccc1)c1ccccc1]
INI-16
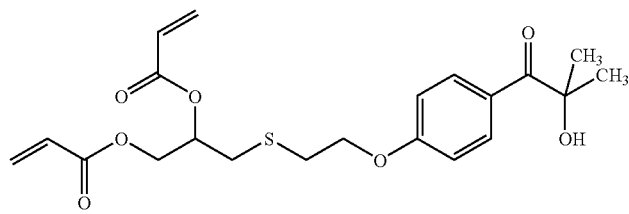 [SMILES: C=CC(=O)OCC(CSCCOc1ccc(C(=O)C(C)(C)O)cc1)OC(=O)C=C]
INI-17
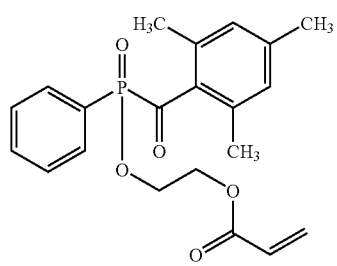 [SMILES: C=CC(=O)OCCOP(=O)(C(=O)c1c(C)cc(C)cc1C)c1ccccc1]
INI-18
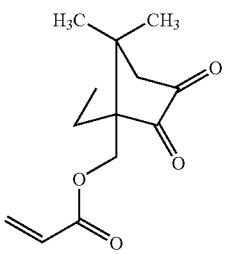 [SMILES: C=CC(=O)OCC1(CC)C(=O)C(=O)CC1(C)C]
INI-19
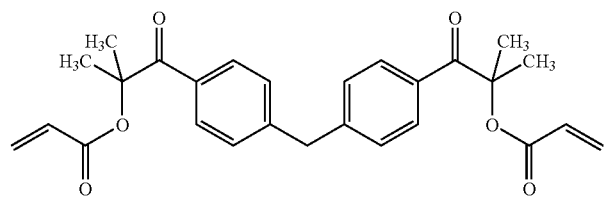 [SMILES: C=CC(=O)OC(C)(C)C(=O)c1ccc(Cc2ccc(C(=O)C(C)(C)OC(=O)C=C)cc2)cc1]
INI-20
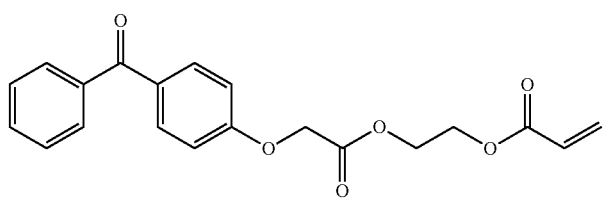 [SMILES: C=CC(=O)OCCOC(=O)COc1ccc(C(=O)c2ccccc2)cc1]

EXAMPLES

Materials

All materials used in the following examples were readily available from Aldrich Chemical Co. (Belgium) unless otherwise specified.

MEK is methyl ethyl ketone.

DAROCUR™ 2959 is a photoinitiator available from CIBA SPECIALTY CHEMICALS

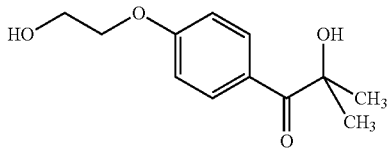

DAROCUR™ 2959

DAROCUR™ 1173 is a photoinitiator available from CIBA SPECIALTY CHEMICALS

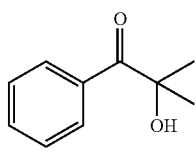

DAROCUR™ 1183

C-hydroxymethylbenzoin can be prepared according to Hageman H., Makromol. Chem., Rapid Commun. 2, 517-521 (1981).

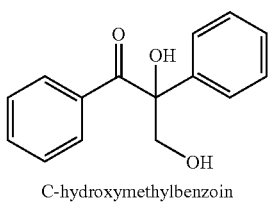 [SMILES: O=C(c1ccccc1)C(O)(CO)c1ccccc1]

C-hydroxymethylbenzoin

Example 1

This example illustrates the superior selectivity and the ease of isolation procedure when using a suspended inorganic base instead of a nitrogen base.

This is exemplified by the synthesis of 4-(2-acryloyloxy-ethoxy)phenyl-2-hydroxy-2-propyl ketone.

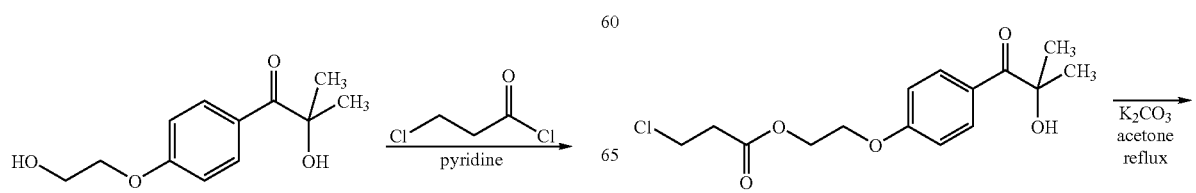

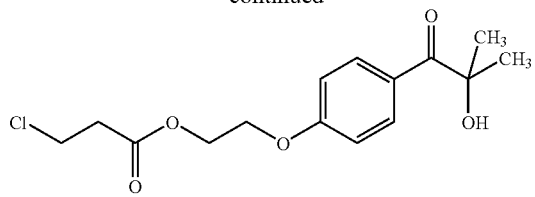

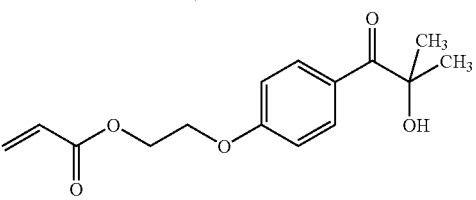

Synthesis of the Intermediate INT-1

INT-1 or 4-(2-(3-chloropropionyloxy)ethoxy)phenyl-2-hydroxy-2-propyl-ketone was prepared as follows:

40.4 g (0.18 mol) 4-(2-hydroxyethoxy)phenyl-2-hydroxy-2-propyl-ketone (DAROCUR™ 2959) was dissolved in 560 ml acetone and 29.1 ml (28.5 g, 0.36 mol) pyridine was added. The reaction mixture was cooled to −10° C. and 34.4 ml (45.7 g, 0.36 mol) 3-chloropropionyl chloride was added over 40 minutes, while the temperature was kept at −10° C. The reaction was allowed to continue for 24 hours at room temperature. 400 ml water and 450 ml ethylacetate was added and the mixture was stirred until all precipitated salts were dissolved. The organic fraction was isolated, dried over $MgSO_4$ and evaporated under reduced pressure. 400 ml hexane was added to the residue and the mixture was stirred for 2 hours. The crude 4-(2-(3-chloropropionyloxy)ethoxy)phenyl-2-hydroxy-2-propyl-ketone precipitated from the medium, was isolated by filtration, washed with hexane and dried. 48.3 g (96%) of 4-(2-(3-chloropropionyloxy)ethoxy)phenyl-2-hydroxy-2-propyl-ketone was isolated. The product was used without further purification to study the elimination.

Evaluation of the Selectivity and the Ease of Isolation Procedure

The prepared intermediate was used to prepare the copolymerizable photoinitiator INI-1. The selectivity of the β-elimination reaction and the ease of isolation of the end product were evaluated using different bases and reaction conditions. The type of base and the number of equivalents used based upon the intermediate is shown by Table 4. The reactions were carried out on a 10 mmol scale and 1 mol % of BHT was added to each reaction mixture to avoid polymerisation.

The synthetic method used is now exemplified for the reaction INV-2, i.e. the β-elimination of the intermediate INT-1 using a dispersion of $K_2CO_3$ in acetone.

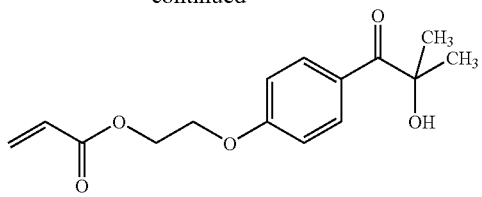

7 g (22 mmol) of 4-(2-(3-chloropropionyloxy)ethoxy)phenyl-2-hydroxy-2-propyl-ketone was dissolved in 70 ml acetone. 4.6 g (33 mmol) $K_2CO_3$ and 50 mg 2,6-di-tert.butyl-4-methylphenol were added. The mixture was refluxed for 3 hours. After cooling down to room temperature, the inorganic salts were removed by filtration and the solvent was removed under reduced pressure. The residue was treated with 75 ml n.-hexane. 4-(2-acryloyloxyethoxy)phenyl-2-hydroxy-2-propyl ketone crystallized from the medium. 4.2 (67.7%) of 4-(2-acryloyloxyethoxy)phenyl-2-hydroxy-2-propyl ketone was isolated.

TABLE 4

| Reaction | Base Type | Eq. | Solvent Type | ml | Reaction conditions |
|---|---|---|---|---|---|
| COMP-1 | Tetramethyl guanidine | 1 | $CH_3CN$ | 35 | 48 hours at room temperature |
| COMP-2 | Tetramethyl guanidine | 2 | MEK | 30 | 8 hours at 70° C. |
| COMP-3 | Tetramethyl guanidine | 2.5 | $CH_3CN$ | 30 | 30 minutes at 70° C. |
| COMP-4 | Triethyl amine | 1 | $CH_3CN$ | 30 | 1.5 h at reflux, followed by 48 hours at room temperature |
| COMP-5 | Triethyl amine | 2 | $CH_3CN$ | 25 | 2 hours room temperature |
| COMP-6 | 1,8-diazabicyclo[5.4.0]undec-7-ene | 1 | $CH_3CN$ | 35 | 30 minutes at room temperature |
| INV-1 | Anhydric $K_2CO_3$ | 1 | Acetone | 70 | 2.5 hours reflux |
| INV-2 | Anhydric $K_2CO_3$ | 1.5 | Acetone | 70 | 3 hours reflux |

The results of the reaction are summarized in Table 5. The % conversion was measured using a GC-method. 200 µl of each sample was diluted with 1 ml $CH_2Cl_2$. 1 µl of each sample was injected. An Alltech EconocapEC5 column was used (30× 0.32 025 µm) at a flow of 2.0 ml/min He and a split ratio of 50:1. The initial temperature was 60° C., which was kept for one minute, followed by a temperature ramp of 35° C. per minute until a maximum temperature of 320° C., which was kept for one and a half minute. An FID (Flame Ionization Detector) was used for detection.

TABLE 5

| Reaction | % conversion | Isolation procedure |
|---|---|---|
| COMP-1 | Incomplete | The reaction was not worked up |
| COMP-2 | 97% | 1. Dilution with 100 ml ethyl acetate<br>2. Extraction with 40 ml 6N HCl<br>3. Dried over MgSO4<br>4. Evaporation under reduced pressure |
| COMP-3 | 100% | 1. Evaporation of CH3CN under reduced pressure<br>2. Addition of 20 ml acetone to remove the salts |

TABLE 5-continued

| Reaction | % conversion | Isolation procedure |
|---|---|---|
| | | 3. Evaporation under reduced pressure<br>4. Multiple crystallization experiments from n.-hexane and methyl tert. butyl ether |
| COMP-4 | 46% | The reaction was not worked up |
| COMP-5 | 98% | 1. Dilution with 75 ml ethyl acetate<br>2. Extraction with 25 ml 0.1N HCl and 75 ml water<br>3. Dried over MgSO4<br>4. Evaporation under reduced pressure<br>5. Treatment with 50 ml n.-hexane |
| COMP-6 | 100% | 1. Diluted with 100 ml ethyl acetate<br>2. Extraction with 50 ml 6N HCl<br>3. Dried over MgSO4<br>4. Evaporation under reduced pressure |
| INV-1 | 98% | 1. Removal of the inorganic salts by filtration<br>2. Evaporation of the solvent under reduced pressure<br>3. Crystallisation from hexane |
| INV-2 | 100% | 1. Removal of the inorganic salts by filtration<br>2. Evaporation of the solvent<br>3. Crystallisation form hexane |

Incomplete conversion of the intermediate to the copolymerizable photoinitiator INI-1 was observed for the reactions COMP-1 and COMP-4, which were consequently not worked up.

Hydrolysis of the photoinitiator INI-1 to the starting material DAROCUR™ 2959 was observed for the reactions COMP-2 and COMP-3. For reaction COMP-2, a hydrolysis of up to 50% was observed based upon the gas chromatographic analysis. In reaction COMP-3, it was not possible to remove all the tetramethyl guanidine salts.

Although a product with a reasonable purity was isolated from the reaction COMP-5, the isolation procedure is not really suitable for production on an industrial scale.

In the reaction COMP-6, full conversion of the intermediate was established, but some additional side products were found to be present in the end product and also incomplete extractive removal of the DBU-salt was observed.

In the reactions INV-1 and INV-2, almost complete or complete conversion was observed and the end product was very easily worked up. No side products could be detected in the photoinitiator prepared by the reaction INV-2.

As a general conclusion from Table 5, it should be clear that, using a fine dispersion of an inorganic base in an aprotic solvent, results in a complete conversion during elimination and an easy isolation procedure, without the formation of side products, while the use of organic nitrogen containing bases, leads or to incomplete conversion when equivalent amounts are used or to more laborious extractive isolation procedure to remove the required excess, often accompanied by the hydrolysis of the end product to DAROCUR™ 2959, or the formation of side products.

Example 2

This example illustrates the influence of the type of inorganic base used on the reaction INV-2 of EXAMPLE 1.

Synthesis

The reactions and the determination of the % conversion were performed in the same way as described in EXAMPLE 1, except that different types of inorganic bases were used in the reaction mixtures according to Table 6 and Table 7. The amount of the components used is given in g, with the exception of acetone which is given in ml. The reactions were carried out in an RS10 parallel reactor (Barstead STEM™) using 1.5 equivalent of inorganic base for 1 equivalent of the intermediate INT-1.

TABLE 6

| Component | Eq. | Amount used (in g) | | | | |
|---|---|---|---|---|---|---|
| | | R1 | R2 | R3 | R4 | R5 |
| INT-1 | 1 | 1.3 | 1.3 | 1.3 | 1.3 | 1.3 |
| $Na_2CO_3$ anh. | 1.5 | 0.6 | — | — | — | — |
| $K_2CO_3$ anh. | 1.5 | — | 0.8 | — | — | — |
| $KHCO_3$ anh | 1.5 | — | — | 0.6 | — | — |
| $Na_2CO_3 \cdot 10H_2O$ | 1.5 | — | — | — | 1.7 | — |
| $Na_3PO_4 \cdot 12H_2O$ | 1.5 | — | — | — | — | 2.3 |
| BHT | | 0.009 | 0.009 | 0.009 | 0.009 | 0.009 |
| Acetone (in ml) | | 13 | 13 | 13 | 13 | 13 |

TABLE 7

| Component | Eq. | Amount used (in g) | | | |
|---|---|---|---|---|---|
| | | R6 | R7 | R8 | R9 |
| INT-1 | 1 | 1.3 | 1.3 | 1.3 | 1.3 |
| NaOAc·$3H_2O$ | 1.5 | 0.8 | — | — | — |
| $K_3PO_4 \cdot 3H_2O$ | 1.5 | — | 1.6 | — | — |
| KOAc anh. | 1.5 | — | — | 0.6 | — |
| $K_2HPO_4$ anh. | 1.5 | — | — | — | 1.0 |
| BHT | 1% | 0.009 | 0.009 | 0.009 | 0.009 |
| Acetone (in ml) | | 13 | 13 | 13 | 13 |

Evaluation

The conversion was determined, using a GC method. 200 μl of each sample was diluted with 1 ml $CH_2Cl_2$. 1 μl of each sample was injected. An Alltech EconocapEC5 column was used (30×0.32 025 μm) at a flow of 2.0 ml/min He and a split ratio of 50:1. The initial temperature was 60° C., which was kept for one minute, followed by a temperature ramp of 35° C. per minute until a maximum temperature of 320° C., which was kept for one and a half minute. An FID (Flame Ionization Detector) was used for detection.

The % conversion is defined as the ratio of the peak area of 4-(2-acryloyloxyethoxy)phenyl-2-hydroxy-2-propyl ketone, determined by the GC method described above, over the sum of the peak area of 4-(2-acryloyloxyethoxy)phenyl-2-hydroxy-2-propyl ketone and 4-(2-(3-chloropropionyloxy)ethoxy)phenyl-2-hydroxy-2-propyl-ketone times 100.

TABLE 8

| Reaction | Base | Reaction time | % conversion |
|---|---|---|---|
| R1 | Anhydric $Na_2CO_3$ | 10 h | 99 |
| R2 | Anhydric $K_2CO_3$ | 6 h | 100 |
| R3 | Anhydric $KHCO_3$ | 10 h | 99 |
| R4 | $Na_2CO_3 \cdot 10H_2O$ | 10 h | 80 |
| R5 | $Na_2PO_412H_2O$ | 10 h | 95 |
| R6 | NaOAc·$3H_2O$ | 10 h | 82 |
| R7 | $K_3PO_4 \cdot 3H_2O$ | 6 h | 100 |
| R8 | Anhydric KOAc | 4 h | 99 |
| R9 | Anhydric $K_3PO_4$ | 4 h | 90 |

From Table 8, it becomes clear that a broad range of different inorganic bases give a reasonable conversion rate. Bases with both sodium and potassium counter ions selectively yield 4-(2-acryloyloxyethoxy)phenyl-2-hydroxy-2-propyl ketone, but potassium counter ions are particularly preferred as they systematically result in a higher conversion rate.

As illustrated by EXAMPLE 1, often the starting material DAROCUR™ 2959 is formed during isolation when using organic nitrogen containing bases. Therefore, 4-(2-acryloyloxyethoxy)phenyl-2-hydroxy-2-propyl ketone was isolated from the reactions R1, R2, R3, R5, R8 and R9. The additional formation of DAROCUR™ 2959 during isolation was measured using GC-analysis. 4-(2-acryloyloxyethoxy)phenyl-2-hydroxy-2-propyl ketone was isolated as follows. The inorganic salts were removed by filtration and the solvent was evaporated under reduced pressure. The residues were treated with 10 ml n.-hexane and isolated again. These samples were analyzed, using the GC-method, described above. The results are summarized in Table 9.

TABLE 9

| Reaction | Base | % additional DAROCUR ™ 2959 formed during isolation |
|---|---|---|
| R1 | Anhydric $Na_2CO_3$ | No detectable increase |
| R2 | Anhydric $K_2CO_3$ | No detectable increase |
| R3 | Anhydric $KHCO_3$ | No detectable increase |
| R5 | $Na_2PO_412H_2O$ | 1.5% |
| R8 | KOAc | No detectable increase |
| R9 | Anhydric $K_3PO_4$ | 0.5% |

From Table 8 and Table 9, it should be clear that the synthetic method according to the present invention systematically leads to a simplified synthetic process, by avoiding laborious extractions to remove the excess of organic nitrogen containing bases required for complete conversion of the 3-chloropropionate to an acrylate. The formation of DAROCUR™ 2959 during isolation was also effectively reduced thereby avoiding the problems often encountered with organic nitrogen containing bases during the elimination and isolation afterwards.

Example 3

This example illustrates that the method according to the present invention is applicable to other initiators. The required intermediates were prepared without optimizing the reaction circumstances.

Synthesis of 4-acryloxybenzophenone (INI-3)

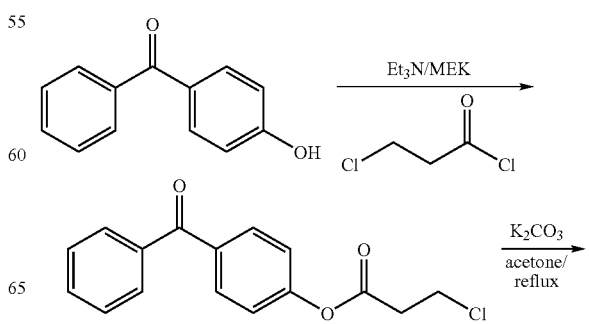

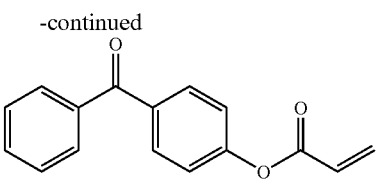

6.7 g (35 mmol) of 4-hydroxy-benzophenone was dissolved in 100 ml methyl ethyl ketone. 4.2 g (42 mmol) triethyl amine was added and the mixture was cooled to −10° C. 5.3 g (42 mmol) 3-chloro-propionyl chloride was added drop wise, while the temperature was kept below −5° C. The reaction was allowed to continue for 30 minutes at 0° C. and 3 hours at room temperature. The precipitated salts were removed by filtration and the solvent was evaporated under reduced pressure. 3-Chloro-propionic acid 4-benzoylphenyl ester was isolated by preparative column chromatography on a Prochrom LC80 column, using n-hexane/ethylacetate 75/25 as eluent at a flow rate of 150 ml/min and Kromasil 60A 10 micron as silica. 1.2 g of 3-chloro-propionic acid 4-benzoylphenyl ester was isolated.

1.2 g (4.75 mmol) 3-chloro-propionic acid 4-benzoylphenyl ester was dissolved in 12 ml acetone. 10 mg BHT and 1 g (7.13 mmol) anhydric $K_2CO_3$ were added. The mixture was refluxed for 2 hours. A TLC analysis (Merck Kieselgel 60$F_{254}$, eluent ethyl acetate/n.-hexane 30/70) indicated a complete conversion of 3-chloro-propionic acid 4-benzoylphenyl ester to 2-propenoic acid 4-benzoylphenyl ester. The inorganic salts were removed by filtration and the solvent was evaporated under reduced pressure. 0.8 g of 2-propenoic acid 4-benzoylphenyl ester was isolated. Based on TLC analysis, there were no indications for the formation of side products. This analysis was confirmed by $^1$H-NMR spectroscopy.

Synthesis of 2-propenoic acid
1,1-dimethyl-2-oxo-2-phenylethyl ester (INI-6)

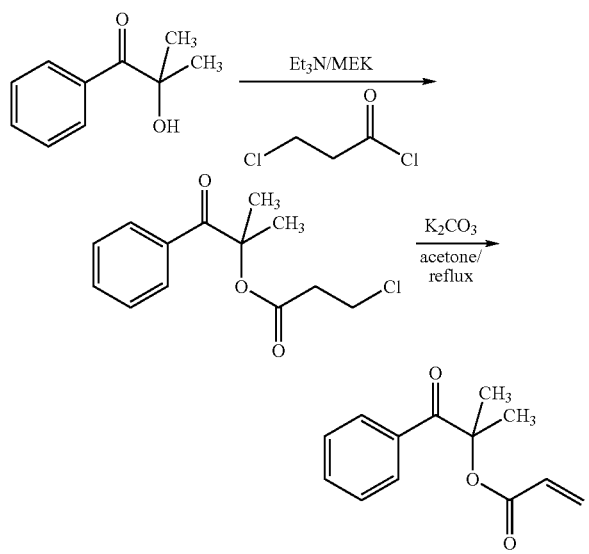

9.9 g (60 mmol) 2-hydroxy-2-methyl-1-phenyl-1-propanone (DAROCUR™ 1173) was dissolved in 60 ml tetrahydrofuran. 6.1 g (60 mmol) triethyl amine was added and the reaction mixture was cooled to −10° C. 7.6 g (60 mmol) 3-chloro-propionyl chloride was added while the temperature was kept below −5° C. The reaction was allowed to continue for 30 minutes at 0° C. and for 72 hours at 40° C. The precipitated salts were removed by filtration and the solvent was evaporated under reduced pressure. 3-chloro-propionic acid 1,1-dimethyl-2-oxo-2-phenylethyl ester was purified by preparative column chromatography on a Prochrom LC80 column, using n.-hexane/ethyl acetate 80/20 as eluent at a flow rate of 150 ml/min and Kromasil 60A 10 micron as silica. 1 g of 3-chloro-propionic acid 1,1-dimethyl-2-oxo-2-phenylethyl ester was isolated.

1 g (3.93 mmol) of 3-chloro-propionic acid 1,1-dimethyl-2-oxo-2-phenylethyl ester was dissolved in 10 ml acetone. 9 mg BHT and 0.8 g (5.9 mmol) anhydric $K_2CO_3$ were added and the mixture was refluxed for 2 hours. A TLC analysis (Merck Kieselgel 60$F_{254}$, eluent ethyl acetate/n.-hexane 30/70) indicated a complete conversion of 3-chloro-propionic acid 1,1-dimethyl-2-oxo-2-phenylethyl ester to 2-propenoic acid 1,1-dimethyl-2-oxo-2-phenylethyl ester. The inorganic salts were removed by filtration and the solvent was removed under reduced pressure. 0.7 g (77.8%) of 2-propenoic acid 1,1-dimethyl-2-oxo-2-phenylethyl ester was isolated as a white crystalline solid. Based on a TLC analysis, there were no indications for the formation of side products. This analysis was confirmed by $^1$H-NMR spectroscopy.

Synthesis of 2-propenoic acid
2-(4-benzoylphenoxy)ethyl ester (INI-7)

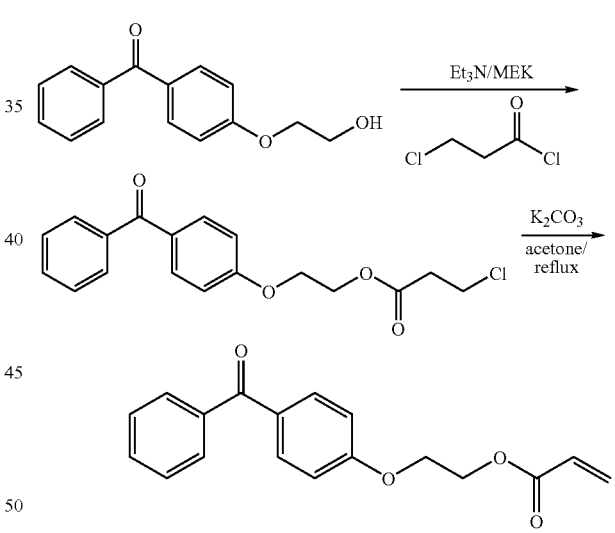

3.6 g (15 mmol) 4-(2-hydroxyethoxy)benzophenone and 1.8 g (18 mmol) triethyl amine were dissolved in 40 ml 2-butanone. The mixture was cooled to −10° C. and 2.3 g (18 mmol) 3-chloro-propionyl chloride was added drop wise while the temperature was kept below −5° C. The reaction was allowed to continue first at 0° C. for 30 minutes, followed by 16 hours at room temperature. The precipitated salts were removed by filtration and the solvent was removed under reduced pressure. The crude 3-chloro-propionic acid 2-(4-benzoylphenoxy)ethyl ester was purified by preparative column chromatography on a Prochrom LC80 column, using n.-hexane/ethyl acetate 70/30 as eluent at a flow rate of 50 ml/min and Kromasil 60A 10 micron as silica. 1.9 g (32%) of 3-chloro-propionic acid 2-(4-benzoylphenoxy)ethyl ester was isolated.

1.9 g (5.7 mmol) 3-chloro-propionic acid 2-(4-benzoylphenoxy)ethyl ester was dissolved in 19 ml acetone. 10 mg BHT and 1.2 g (8.55 mmol) anhydric K₂CO₃ were added and the mixture was refluxed for 3 hours. A TLC analysis (Merck Kieselgel 60F$_{254}$, eluent ethyl acetate/n.-hexane 30/70) indicated a complete conversion of 3-chloro-propionic acid 2-(4-benzoylphenoxy)ethyl ester to 2-propenoic acid 2-(4-benzoylphenoxy)ethyl ester. The inorganic salts were removed by filtration and the solvent was removed under reduced pressure. 1.4 g (82.4%) of 2-propenoic acid 2-(4-benzoylphenoxy)ethyl ester was isolated. Based on a TLC analysis, there were no indications for the formation of side products. This analysis was confirmed by ¹H-NMR spectroscopy.

Synthesis of 2,3-diphenyl-2-hydroxy-3-oxopropyl acrylate (INI-15)

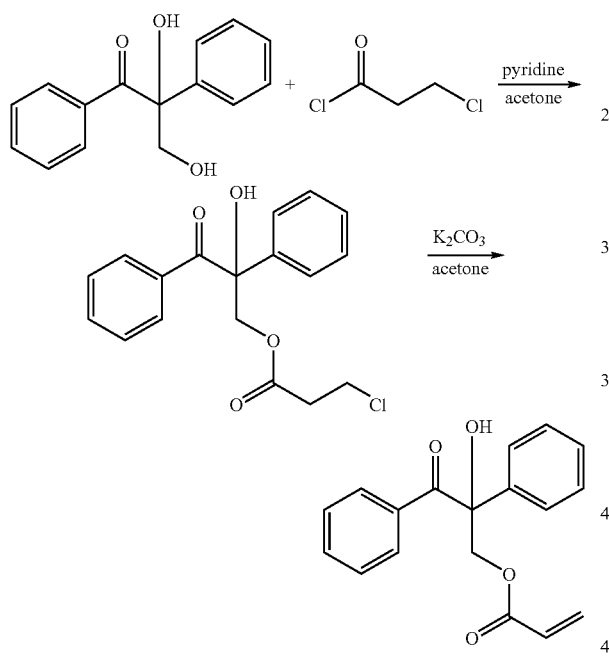

Synthesis of (2,3-diphenyl-2-hydroxy-3-oxopropyl)-3-chloro-propionate (INT-16)

10.2 g (42 mmol) 2,3-dihydroxy-1,2-diphenyl-1-propanone was dissolved in 130 ml acetone. 6.6 g (84 mmol) pyridine was added and the reaction mixture was cooled to −10° C. 10.7 g (84 mmol) 3-chloropropionyl chloride was added drop wise, while the temperature was kept below 0° C. The reaction was allowed to continue for 30 minutes at 0° C., followed by 5 hours at room temperature. 150 ml ethyl acetate and 200 ml water were added to the reaction mixture. The organic fraction was isolated and the aqueous fraction was extracted for a second time with 200 ml ethyl acetate. The pooled organic fractions were dried over MgSO₄ and evaporated under reduced pressure. (2,3-diphenyl-2-hydroxy-3-oxopropyl)-3-chloro-propionate was isolated by preparative column chromatography on a Prochorm LC80 column, using Kromasil Si60A 10μ and methylene chloride as eluent at a flow rate of 150 ml/min. 8 g of (2,3-diphenyl-2-hydroxy-3-oxopropyl)-3-chloro-propionate (60%) was isolated as a white crystalline product. (TLC on Merck Kieselgel 254F$_{60}$, eluent methylene chloride, R$_f$: 0.19)

Synthesis of 2,3-diphenyl-2-hydroxy-3-oxopropyl acrylate (INI-1)

7.8 g (23.4 mmol) (2,3-diphenyl-2-hydroxy-3-oxopropyl)-3-chloro-propionate was dissolved in 75 ml acetone. 4.9 g (35.1 mmol) K₂CO₃ and 50 mg BHT were added and the mixture was refluxed for 5 hours. The inorganic salts were removed by filtration and the solvent was evaporated under reduced pressure. The residue was treated with 50 ml n.-hexane, 2,3-diphenyl-2-hydroxy-3-oxopropyl acrylate was isolated by filtration and dried. 6.3 g of 2,3-diphenyl-2-hydroxy-3-oxopropyl acrylate (91%) was isolated. Based on ¹H-NMR-analysis the conversion proved to be 98%.

Synthesis of 3-chloro-propionic acid 9-oxo-9H-thioxanthen-2-yl ester (INT-4)

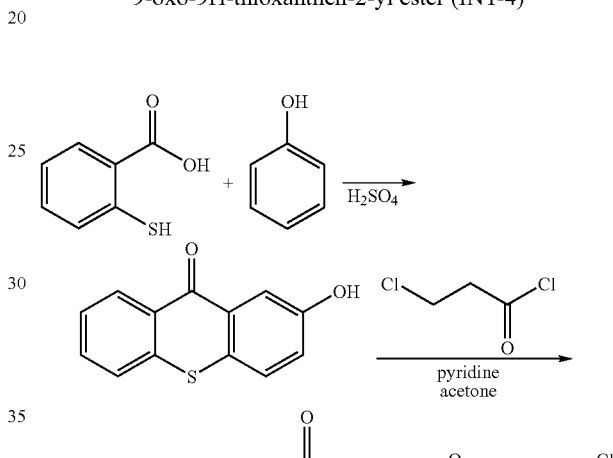

Synthesis of 2-hydroxy-9H-thioxanthen-9-one 150 ml concentrated sulfuric acid was added to 16 g (0.103 mol) thiosalicylic acid. 60 g (0.44 mol) phenol was added portion wise. The temperature rose to 50° C. during the addition. The mixture was allowed to cool down to room temperature and stirred for 30 minutes at room temperature. The mixture was heated to 80° C. for 48 hours. The mixture was allowed to cool down to room temperature and carefully added over one hour to 3 l water at 75° C. The mixture was stirred for an additional hour at 60° C. and allowed to cool down to room temperature. 2-hydroxy-9H-thioxanthen-9-one was isolated by filtration and dried. 12.9 g of 2-hydroxy-9H-thioxanthen-9-one (55%) was isolated. 2-hydroxy-9H-thioxanthen-9-one was sufficiently pure to be used without further purification.

Synthesis of 3-chloro-propionic acid 9-oxo-9H-thioxanthen-2-yl ester 5 g (22 mmol) of 2-hydroxy-9H-thioxanthen-9-one was dissolved in 200 ml refluxing acetone. 3.6 ml (3.5 g, 44 mmol) pyridine was added, followed by the addition of 5.6 g (44 mmol) 3-chloropropionyl chloride. The mixture was refluxed for 5 hours. The solvent was removed under reduced pressure, after cooling down to room temperature and the residue was dissolved in 200 ml methylene chloride. The methylene chloride was extracted with 150 ml of a 1 M Na$_2$CO$_3$ solution and 150 ml of a 0.1 N hydrochloric acid solution. The organic fraction was dried over MgSO$_4$ and evaporated under reduced pressure. 3-chloro-propionic acid 9-oxo-9H-thioxanthen-2-yl ester was isolated by preparative column chromatography on a SVP D40 Merck NP column, using a gradient elution from methylene chloride (20 minutes isocratic elution) to methylene chloride/ethyl acetate 80/20 over 30 minutes and a flow rate of 50 ml/min. 0.414 g of 3-chloro-propionic acid 9-oxo-9H-thioxanthen-2-yl ester (6%) was isolated as a white crystalline compound.

Synthesis of phenyl(2,4,6-trimethylbenzoyl)-phosphinic acid 2-(3-chloropropionylxo)ethyl ester (INT-18)

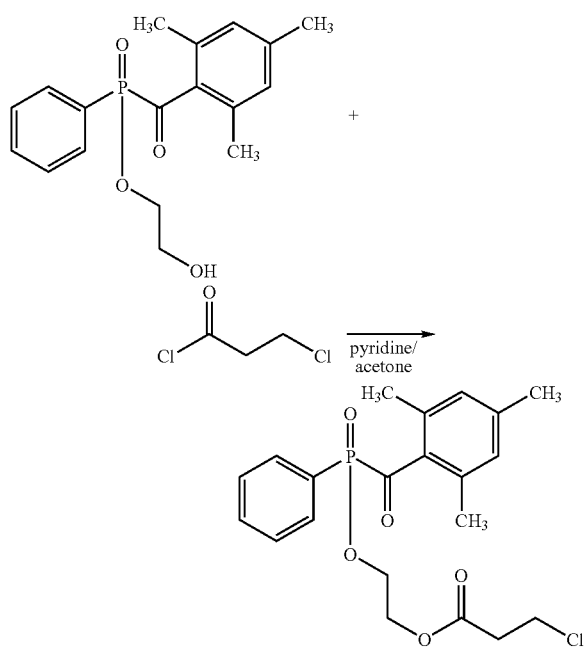

Phenyl(2,4,6-trimethylbenzoyl)-phosphinic acid 2-hydroxyethyl ester can be prepared according to example 3 of DE 10706097 (BASF).

0.22 g (0.66 mmol) phenyl(2,4,6-trimethylbenzoyl)-phosphinic acid 2-hydroxyethyl ester was dissolved in 5 ml acetone. 0.11 ml (1.33 mmol) pyridine and 0.17 g (1.33 mmol) 3-chloropropionyl chloride were added and the mixture was refluxed for 16 hours. The precipitated salts were removed by filtration and 15 ml ethyl acetate was added. The mixture was extracted with 20 ml of a 0.1N HCl solution. The organic fraction was dried over MgSO$_4$ and the solvent was evaporated under reduced pressure. Phenyl(2,4,6-trimethylbenzoyl)-phosphinic acid 2-(3-chloropropionylxo)ethyl ester was isolated by preparative column chromatography on a Prochrom LC80 column, using Kromasil 60A 10µ as silica and methylene chloride/ethyl acetate 90/10 as eluent at a flow rate of 150 ml/min. 0.045 g of phenyl(2,4,6-trimethylbenzoyl)-phosphinic acid 2-(3-chloropropionylxo)ethyl ester was isolated.

Example 4

This example illustrates that not only a chloride can be used as leaving group. This is exemplified by using 3-bromo-propionyl chloride in the synthesis of 4-(2-acryloyloxyethoxy)phenyl-2-hydroxy-2-propyl ketone.

Synthesis of 4-(2-acryloyloxyethoxy)phenyl-2-hydroxy-2-propyl ketone (INI-1)

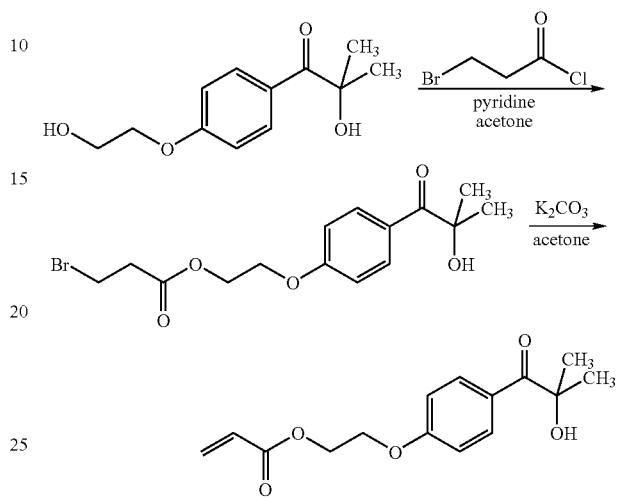

Step 1: Synthesis of INT-15

10.1 g (45 mmol) 2-hydroxy-1-[4-(2-hydroxyethoxy)phenyl]-2-methyl-1-propanone was dissolved in 140 ml acetone. 7.1 g (90 mmol) pyridine was added and the reaction mixture was cooled to −10° C. 16.2 g (90 mmol) 3-bromopropionyl chloride was added drop wise while the temperature was kept below 0° C. The reaction was allowed to continue at 0° C. for 30 minutes, followed by 5 hours at room temperature. 200 ml water and 150 ml ethyl acetate were added to the reaction mixture. The organic fraction was isolated and the aqueous fraction was extracted with 200 ml ethyl acetate. The pooled organic fractions were dried over MgSO$_4$ and evaporated under reduced pressure. 4-(2-(3-bromopropionyloxy)ethoxy)phenyl-2-hydroxy-2-propyl ketone was isolated by preparative column chromatography on a Prochrom LC80 column, using Kromasil 60A 10µ as silica and n.-hexane/ethyl acetate 72/28 as eluent at a flow rate of 150 ml/min. 5.4 g of 4-(2-(3-bromopropionyloxy)ethoxy)phenyl-2-hydroxy-2-propyl ketone (33%) was isolated as a white crystalline product (TLC on Merck Kieselgel 254F$_{60}$, eluent n.-hexane/ethyl acetate 40/60, R$_f$: 0.25)

Step 2: Synthesis of INI-1

5.2 g (14.5 mmol) 4-(2-(3-bromopropionyloxy)ethoxy)phenyl-2-hydroxy-2-propyl ketone was dissolved in 45 ml acetone. 30 mg BHT and 3.0 g (21.75 mmol) K$_2$CO$_3$ were added and the reaction mixture was refluxed for 5 hours. The reaction mixture was allowed to cool down to room temperature and the inorganic salts were removed by filtration. The solvent was removed under reduced pressure and the residue was treated with 50 ml n.-hexane. 4-(2-acryloyloxyethoxy)phenyl-2-hydroxy-2-propyl ketone was isolated by filtration. 3 g of 4-(2-acryloyloxyethoxy)phenyl-2-hydroxy-2-propyl ketone (75%) was isolated as a white crystalline compound.

Example 5

This example illustrates the feasibility of the acylation of hydroxy substituted photoinitiators with 3-chloropropionyl chloride, using a fine dispersion of an inorganic base in an aprotic solvent, directly followed by the elimination to the corresponding acrylate under the same conditions without first isolating the intermediate. This 'one reaction vessel' procedure is particularly advantageous for manufacturing copolymerizable photoinitiators on an industrial scale.

Synthesis of 4-(2-acryloyloxyethoxy)phenyl-2-hydroxy-2-propyl ketone (INI-1)

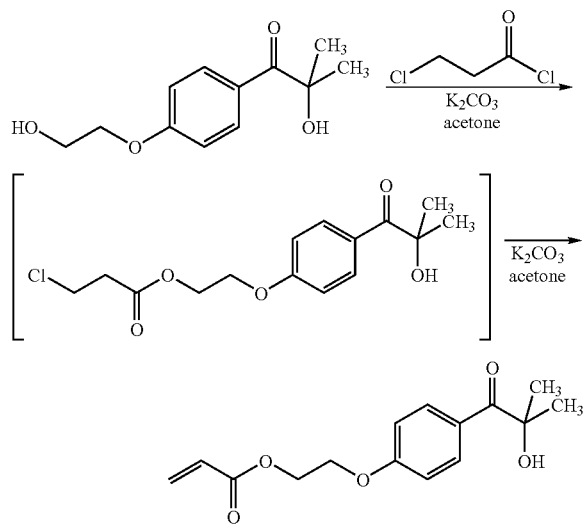

5.6 g (25 mmol) 2-hydroxy-1-[4-(2-hydroxyethoxy)phenyl]-2-methyl-1-propanone and 60 mg BHT were dissolved in 100 ml acetone. 19 g (0.1375 mol) $K_2CO_3$ was added and the reaction mixture was cooled to −5° C. 9.5 ml (12.7 g, 0.1 mol) 3-chloropropionyl chloride was added over 30 minutes. The reaction mixture was refluxed for 10 hours and the conversion of 2-hydroxy-1-[4-(2-hydroxyethoxy)phenyl]-2-methyl-1-propanone to 4-(2-acryloyloxyethoxy)phenyl-2-hydroxy-2-propyl ketone was determined by GC as disclosed above. After 10 hours, the conversion proved to be 94.3%. Conventional isolation procedure can be used to isolate 4-(2-acryloyloxyethoxy)phenyl-2-hydroxy-2-propyl ketone.

Synthesis of 2-propenoic acid 9-oxo-9H-thioxanthen-2-yl ester (INI-4)

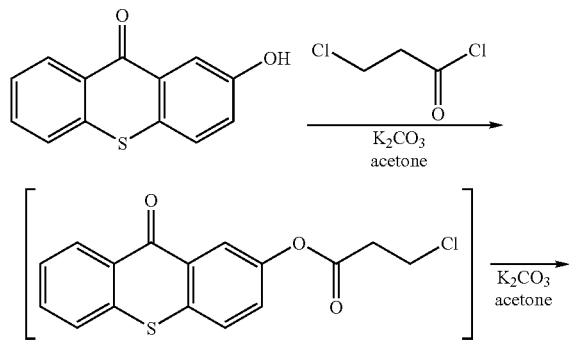

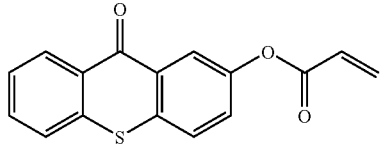

5 g (22 mmol) 2-hydroxy-9H-thioxanthen-9-one was dissolved in 100 acetone. 50 mg BHT, 10.6 g 77 (mmol) $K_2CO_3$ and 5.6 g (44 mmol) 3-chloropropionyl chloride were added. The mixture was refluxed for 3 hours. The salts were removed by filtration after cooling down to room temperature and the solvent was removed under reduced pressure. The residue was treated with 100 ml water and the crude 2-propenoic acid 9-oxo-9H-thioxanthen-2-yl ester was isolated by filtration. 2-propenoic acid 9-oxo-9H-thioxanthen-2-yl ester was further purified using preparative column chromatography on a Prochrom LC80 column, using Kromasil Si 60A 10μ as silica and methylene chloride as eluent at a flow rate of 150 ml/min. 1.16 g of 2-propenoic acid 9-oxo-9H-thioxanthen-2-yl ester (19%) was isolated. The isolated compound had a purity of 99%. This analysis was confirmed by $^1$H-NMR spectroscopy.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. An intermediate for preparing (meth)acrylated photoinitiators according to Formula (I):

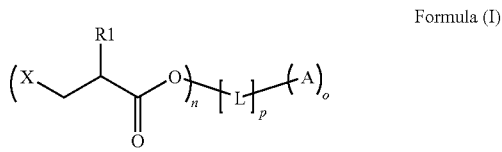

Formula (I)

wherein:

R1 is selected from the group consisting of hydrogen and a methyl group;

A represents a group including at least one photoinitiating moiety selected from the group consisting of benzil ketals, α,α-dialkoxyacetophenones, α-hydroxyalkylphenones, α-aminoalkylphenones, acylphosphine oxides, bis-acylphosphine oxides, acylphosphine sulfides, α-haloketones, α-halosulfones, phenylglyoxalates, and thioxanthones;

L represents a n+o-valent linking group including at least one carbon atom, but containing not more than 20 carbon atoms;

n and o each independently represent an integer from 1 to 4;

p is equal to 1;

X represents a group selected from the group consisting of Cl, Br, I, and $R^2SO_3$; and $R^2$ represents an optionally substituted group selected from the group consisting of an alkyl group, an alkenyl group, an alkynyl group, an alkaryl group, an aralkyl group, an aryl group, and a heteroaryl group.

2. An intermediate for preparing (meth)acrylated photoinitiators according to Formula (I):

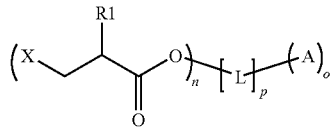

Formula (I)

wherein:

R1 is selected from the group consisting of hydrogen and a methyl group;

A represents a group including at least one photoinitiating moiety selected from the group consisting of benzil ketals, α,α-dialkoxyacetophenones, α-hydroxyalkylphenones, α-aminoalkylphenones, acylphosphine oxides, bis-acylphosphine oxides, acylphosphine sulfides, α-haloketones, α-halosulfones, phenylglyoxalates, thioxanthones, and 1,2-diketones;

L represents a n+o-valent linking group including at least one carbon atom, but containing not more than 20 carbon atoms;

p is equal to 1;

X represents a group selected from the group consisting of Cl, Br, I, and $R^2SO_3$;

$R^2$ represents an optionally substituted group selected from the group consisting of an alkyl group, an alkenyl group, an alkynyl group, an alkaryl group, an aralkyl group, an aryl group, and a heteroaryl group; and n and o are equal to 1.

3. An intermediate for preparing (meth)acrylated photoinitiators according to Formula (I):

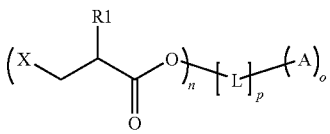

Formula (I)

wherein:

R1 is selected from the group consisting of hydrogen and a methyl group;

A represents a group including at least one photoinitiating moiety selected from the group consisting of benzil ketals, α,α-dialkoxyacetophenones, α-hydroxyalkylphenones, α-aminoalkylphenones, acylphosphine oxides, bis-acylphosphine oxides, acylphosphine sulfides, α-haloketones, α-halosulfones, phenylglyoxalates, thioxanthones, and 1,2-diketones;

n and o each independently represent an integer from 1 to 4;

p is equal to 1;

X represents a group selected from the group consisting of Cl, Br, I, and $R^2SO_3$;

$R^2$ represents an optionally substituted group selected from the group consisting of an alkyl group, an alkenyl group, an alkynyl group, an alkaryl group, an aralkyl group, an aryl group, and a heteroaryl group; and the linking group L links the at least one photoinitiating moiety A to the oxygen atom via a functional group selected from the group consisting of an ester, an amide, an ether, a thioether, and an amine.

4. The intermediate according to claim 1, wherein the linking group L is selected from the group consisting of a substituted or unsubstituted alkylene group, a substituted or unsubstituted arylene group, and a substituted or unsubstituted heteroarylene group.

5. The intermediate according to claim 4, wherein the linking group L is an alkylene group.

* * * * *